United States Patent [19]

Nestor et al.

[11] 4,210,147
[45] Jul. 1, 1980

[54] HEAD TOURNIQUET HAVING INCISION CLOSING CAPABILITY

[75] Inventors: Jack Nestor, 1496 Mayflower Ave., 10461; John W. Devine, Jr., both of Miami, Fla.

[73] Assignee: Nestor Engineering Associates, Inc., Miami, Fla.

[21] Appl. No.: 917,089

[22] Filed: Jun. 19, 1978

[51] Int. Cl.² ............................................. A61B 17/12
[52] U.S. Cl. .................................................... 128/327
[58] Field of Search ............... 128/327, 163, 97, 76 R, 128/303 R, 118, 112, 132 D, 335, 325

[56] References Cited

U.S. PATENT DOCUMENTS

| | | | |
|---|---|---|---|
| 1,317,319 | 9/1919 | Robinson | 128/327 |
| 2,206,481 | 7/1940 | Luchs et al. | 128/163 X |
| 2,444,161 | 6/1948 | Hanafin | 128/327 |
| 3,159,160 | 12/1964 | Ullom | 128/97 |
| 3,659,609 | 5/1972 | Arouete | 128/325 |
| 4,134,398 | 1/1979 | Scrivens | 128/132 D |

FOREIGN PATENT DOCUMENTS 488811 11/1918 France .................................. 128/327

Primary Examiner—William E. Kamm
Assistant Examiner—Michael H. Thaler
Attorney, Agent, or Firm—Erwin M. Barnett

[57] ABSTRACT

A head encircling tourniquet comprises a frame section for surrounding a work area of the scalp connected to an opposing pneumatic pressure applying section by a pair of headsize adjustable members. The frame section has a scalp contacting, uniform pressure applying, liner and is formed with a relatively large central opening providing access to the work area while the frame section and liner controls hemostasis in the work area by pressure exerted by the pneumatic section. Opposite elongated longitudinal sides of the frame and liner are resiliently movable toward each other to close an incision or wound located in the work area for suturing while the tourniquet remains in operative position on the head.

7 Claims, 7 Drawing Figures

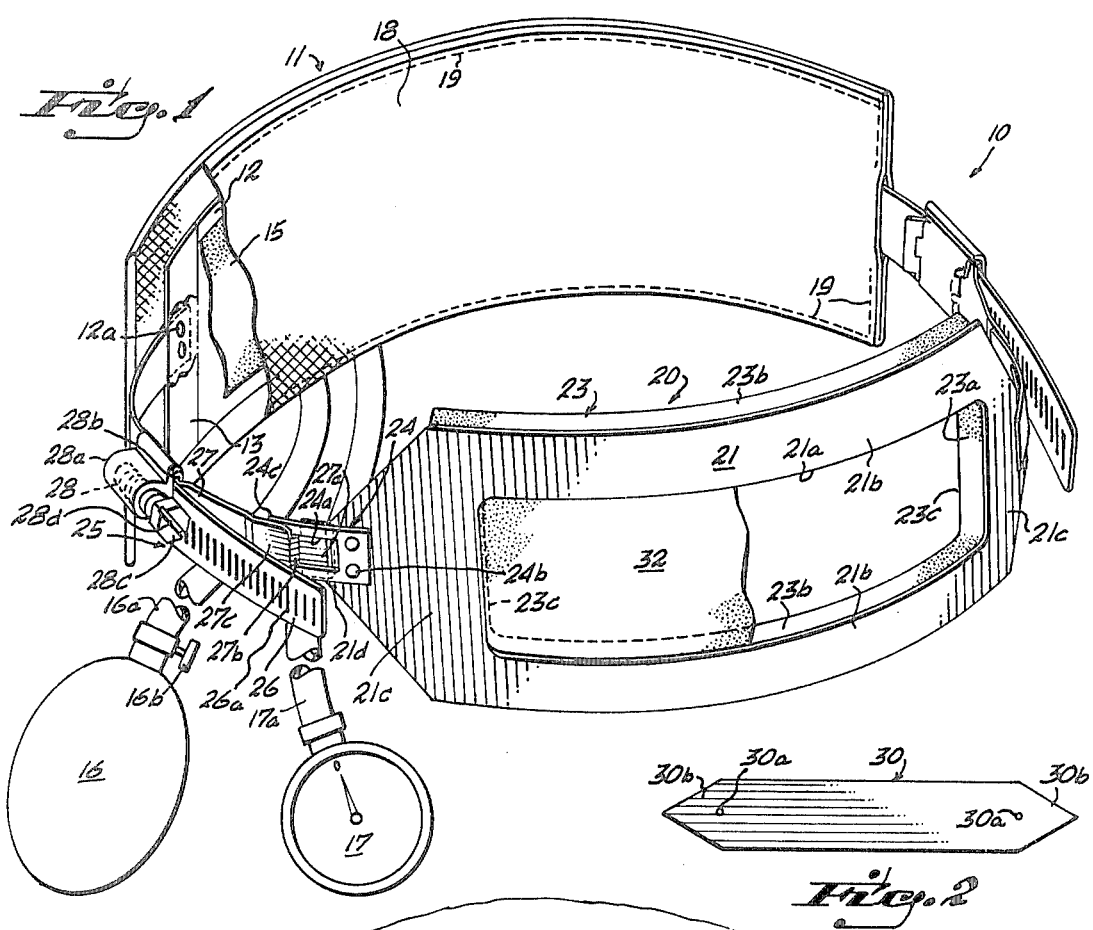
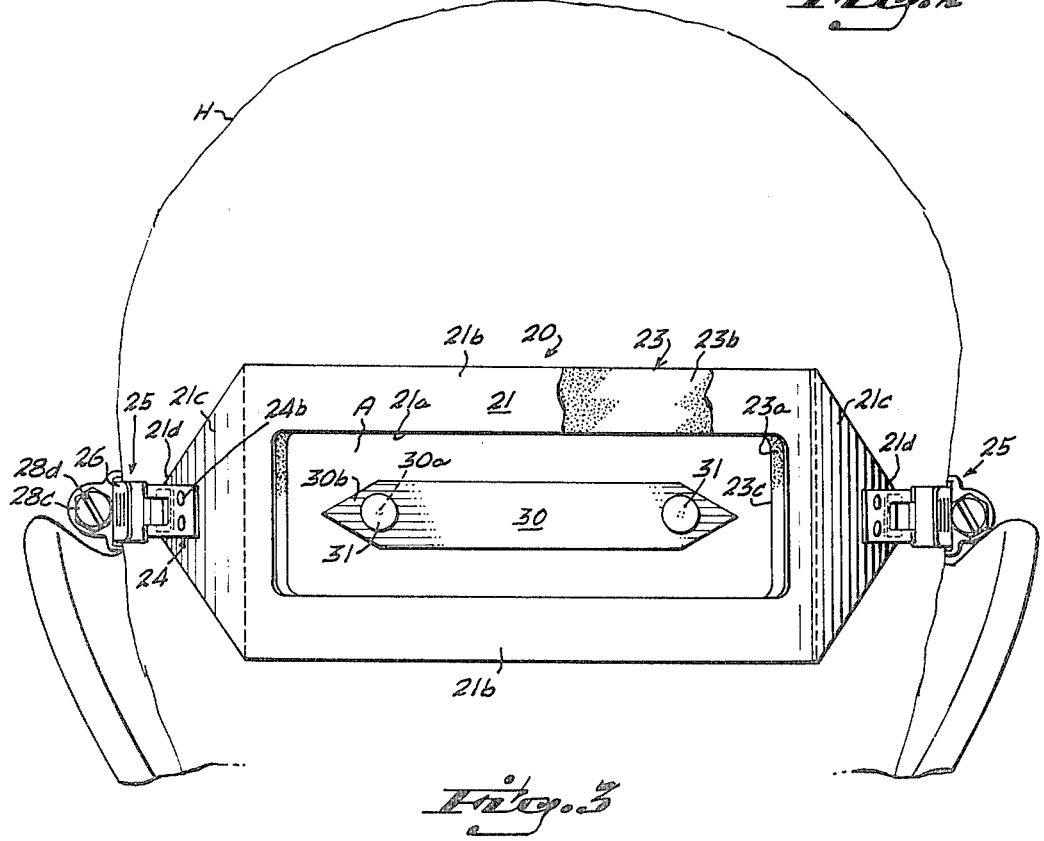

HEAD TOURNIQUET HAVING INCISION CLOSING CAPABILITY

BACKGROUND OF THE INVENTION

1. Field of the Invention

This invention relates generally to hemostasis and more particularly is directed to a head encircling tourniquet for applying pressure by pneumatic means to control bleeding in a desired work area of the scalp while affording maximum surgical exposure to the work area and having resilient means enabling closure and retention in a closed condition of surgical incisions or wounds within the work area for suturing while the tourniquet remains in position on the head.

2. Description of the Prior Art

Head tourniquets may be simply a rubber band wound about the head, affording no control of pressure and indiscriminately cutting off the supply of blood. More sophisticated tourniquets utilizing sectionalized, size adjustable, head bands with pneumatic pressure control have been used but, as constructed, afford only a restricted work area, particularly those intended for scalp surgery, such as, for the removal of donor graft strips for hair transplant, and require removal of the tourniquet, and hence loss of time as well as of all hemostatic control, while the incision is being closed and sutured. Scalp wounds under emergency conditions are difficult to suture without an easy to operate and effective tourniquet to achieve hemostasis and provide adequate visibility of the wound.

There is, therefore, a compelling need to generally solve the problem of hemostasis in scalp surgery and scalp wound repair by a quick acting, gaugeable, pneumatic pressure operated tourniquet which will control the blood flow of a predetermined work area of the scalp, yet provide adequate circulation to the remainder of the scalp, and which will incorporate means whereby the incision or wound may be closed and sutured while the tourniquet is retained in an operative position.

SUMMARY OF THE INVENTION

Among the objects of the invention is to provide for hemostasis in a selected area of the scalp by a sectionalized, head size adjustable, pneumatic pressure controlled tourniquet which will maintain such area in an exposed, readily accessible condition for performing therein various surgical procedures, such as, removal of scalp tumors, and in particular shall facilitate the currently preferred hair transplant technique. This technique utilizes the selected area of the scalp as the donor area for the hair transplant from which an elongated strip of hair follicle bearing skin is removed and cut into square plugs for transfer to square cut holes prepared in the recipient area of the scalp. The donor area, after removal of the strip and with the aid of the tourniquet and while the latter remains in position, is closed by stretching the scalp to bring the opposite longitudinal edges of the excised scalp together and is sutured to leave a straight line scar which will be readily concealed by the hair.

The tourniquet embodying the invention features a head encircling band comprising two flexible plate members arranged opposite each other and interconnected at opposite ends thereof by a pair of easily manipulatable head or circumferential size-adjusting means. One of the plate members forms a backing for and supports an air bladder provided with an air pressure gauge and a valved, hand operated bulb for inflating and deflating the bladder to exert a desired pressure by the tourniquet. The other plate member is formed as a frame having a relatively large center area cut out to provide a window exposing the underlying scalp area when the tourniquet is in operative position. A relatively firm, flexible and resilient rubber pad liner is attached to the interior side of the frame whereby pressure controlled by the gauged air bladder is evenly applied to the scalp surrounding the area exposed by the window to provide hemostasis in that area during surgery therein. The longitudinal sides of the frame, which are substantially longer than the transverse sides thereof, are flexible in a medial direction while the transverse sides are flexible for slight outward bowing whereby the rubber liner of the longitudinal sides of the frame contacts and grips the underlying scalp enabling the free edges of an excision cut from the exposed scalp area to be brought together and closed for suturing by the medial flexure of the longitudinal sides of the frame.

BRIEF DESCRIPTION OF THE DRAWINGS

FIG. 1 is a perspective view of the tourniquet embodying the invention showing, at the rear, a pneumatic pressure applying and controlling section connected at opposite ends by length adjusting tapes to a hemostatic frame section, parts of the rear section being broken away to show interior construction, and a removable pad, partly broken away, being shown in position in the window of the hemostatic frame section.

FIG. 2 is a plan view of a template for marking the outline of the skin graft to be removed from a donor site in performing a hair transplant utilizing the tourniquet embodying the invention.

FIG. 3 is an elevational view of the back of a hair transplant patient's head showing the hemostatic frame section of the tourniquet in FIG. 1 mounted in position surrounding a donor area of the scalp, the template of FIG. 2 being shown mounted on the scalp by fixation tacks preparatory to marking the outline thereof on the scalp to designate the strip graft to be excised.

DESCRIPTION OF THE PREFERRED EMBODIMENT

Figure 4:
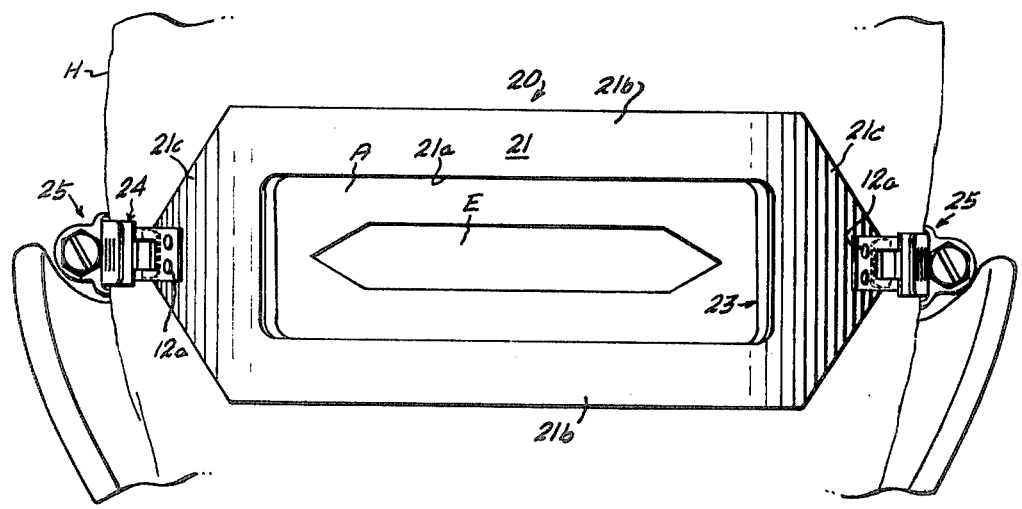
FIG. 4 is a view similar to FIG. 3 but showing the donor area after the donor strip graft has been excised.

Referring in detail to the drawings, 10 generally denotes a head tourniquet constructed to embody the invention, seen in FIG. 1 to comprise a pneumatic pressure applying and controlling section 11 arranged to oppose a hemostatic frame section 20, which sections 11 and 20 are interconnected by a pair of circumferential size-adjusting tapes 25.

Section 11 comprises a thin relatively flexible backing plate 12 and an air bladder 15 extending along the interior surface of plate 12, both enclosed in a fabric covering or envelope 18 having front and rear panels suitably joined together by stitched peripheral seam 19. Attached to each opposite end of backing plate 12, at the midline thereof and by suitable means, such as rivets 12a, is the adjustable length strip element 26 of each size-adjusting tape 25, which strip elements 26 extend in opposite directions through suitable openings in stitched seam 19. An adhesive tape 13 may be wound around the opposite end portions of backing plate 12 as a covering for rivets 12a.

Air bladder 15 is provided with a pair of tubes 16a and 17a which also extend through suitable openings in stitched seam 19 and are preferably located along a longitudinal side of section 11. Tubes 16a and 17a communicate with the interior air chamber of air bladder 15 and, respectively, terminate in hand pump bulb 16 and air pressure gauge 17. Bulb 16 may be equipped with a suitable valve operated by thumb screw 16b for deflating air bladder 15. Air bladder 15, bulb 16 and pressure gauge 17 are similar in construction and operation to those well known and used in sphygmomanometers.

Hemostatic frame section 20 comprises a thin, relatively flexible frame 21 formed with a relatively large central opening 21a and a resilient rubber pad liner 23 likewise having a central opening 23a conforming in size and shape to opening 21a. Central openings 21a and 23a serve as a window, hereinafter designated window 21a, 23a, which defines and affords free access to a surgical work area A of the underlying scalp to which hemostasis is provided by frame section 20 when tourniquet 10 is applied to a patient's head H in the manner hereinafter described. Frame 21 is preferably longitudinally elongated to provide window 21a, 23a in a rectangular shape and has opposite longitudinal frame portions 21b and opposite transverse frame portions 21c, each of the latter tapering from an end of liner 23 to a medially located attachment end 21d, as will be clear from FIGS. 1 and 2. Liner 23, which is attached to the interior surface of frame 21 by a suitable adhesive, has opposite longitudinal sides 23b and opposite transverse sides 23c, all substantially the same width, namely, the width of frame portions 21b.

In order to snugly fit tourniquet 10 to the patient's head H and maintain sections 11 and 20 substantially in symmetrical opposition, a pair of circumferential size-adjusting means of suitable construction may be provided, each having dependable, fine adjustment capability with manipulating means preferably readily accessible from the hemostatic frame section 20 side of tourniquet 10. To this end, circumferential size-adjusting tapes 25 are provided deriving their adjustability from a worm gear and slotted tape interengagement similar to that of the well known metal hose clamp construction. Thus, each tape 25 comprises the hereinbefore mentioned adjustable length strip element 26 which is formed with uniformly spaced transverse slots 26a and a fixed length strip element 27 which is connected to an attachment end 21d of frame 21 in the manner hereinafter described. A worm gear 28 is mounted for rotation in housing 28a which is suitably secured to the free end of fixed length strip element 27 and provides a passageway 28b through which element 26 is fed by engagement of worm gear 28 in transverse slots 26a, in the well understood manner. An end of worm gear 28 projects from housing 28a in a direction toward hemostatic frame section 20 and is formed with a conventional hexagonal head 28c for wrench engagement and a diametric groove 28d for screwdriver engagement, either tool serving to rotate worm gear 28 and thereby finely adjust the effective length of adjustable length strip element 26.

Figure 5:
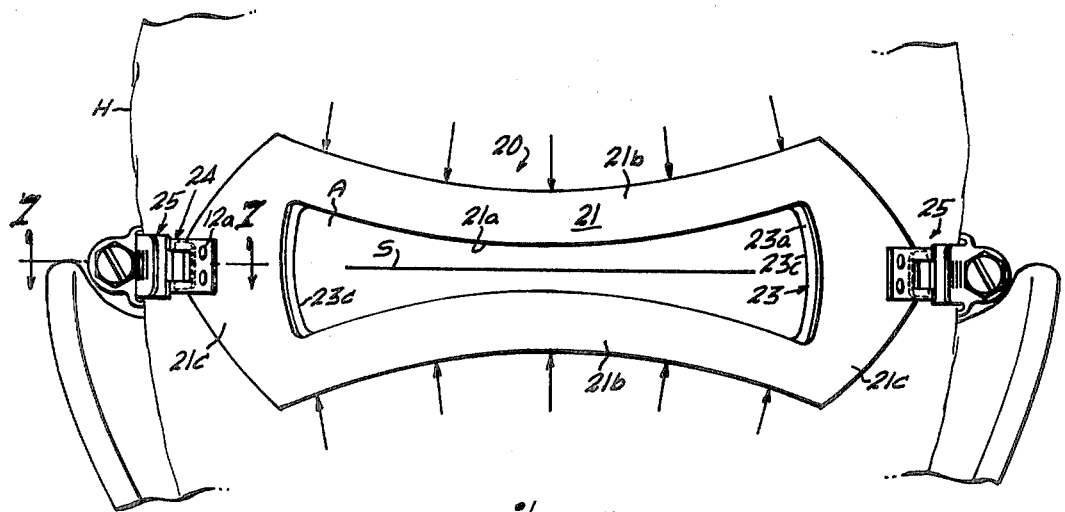
FIG. 5 is a view similar to FIG. 4 but showing the longitudinal sides of the hemostatic frame section deformed medially as indicated by the arrows bringing the edges of the excision together preparatory to and during the suturing thereof.
Figure 7:
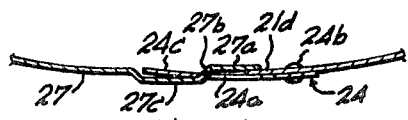
FIG. 7 is a sectional view taken on line 7—7 in FIG. 5 showing details of the mounting of the fixed length strip element of the size adjusting tape providing pivotal adjustability of the hemostatic frame section.

Each fixed length strip 27 may be suitably connected to an attachment end 21d of frame 21 to provide angular adjustability whereby the entire hemostatic frame section 20 may swivel at opposite ends thereof with respect to the longitudinal axis of tapes 25 and section 11 providing greater adjustability to ensure proper contact of liner 23 with the contour of the patient's scalp surrounding surgical work area A. For this purpose, as seen in FIGS. 1, 5 and 7, a link 24 having a rectangular cutout 24a is fixedly secured to each attachment end 21d of frame 21 by rivets 24b. Spaced inwardly of an end portion 27a of each fixed length strip element 27 is a pair of transversely aligned notches providing a narrow neck 27b which extends through cutout 24a and connects end portion 27a, located on the interior side of link 24, to a slightly outwardly offset portion 27c, located on the exterior side of link 24 and being sized and shaped to seat the underlying end portion 24c of link 24 which extends beyond cutout 24a. The loose connection afforded by the engagement of each neck 27b in its respective cutout 24a on opposite ends of section 20 enables the latter to swivel with respect to tapes 25.

Whereas the diagonal dimension of cutout 24a permits end portion 27a of element 27 to pass therethrough in assembling link 24 with the latter, permanent assembly of the swiveling connection between link 24 and element 27 may be provided by riveting link 24 to frame 21 so that an end portion of attachment end 21d overlies a portion of cutout 27a, as seen in FIGS. 1 and 7, reducing the effective diagonal dimension of cutout 24a thereby preventing end portion 27a from returning through cutout 24a to disconnect from link 24.

Figure 6:
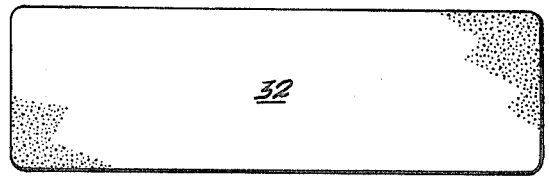
FIG. 6 is a plan view of the pad removed from the window shown in FIG. 1.

Backing plate 12, flexible frame 21 and the components of size-adjusting tapes 25 may all be made of non-corrosive stainless steel. In forming liner 23, as by stamping from a relatively firm yet flexible and resiliently compressible gum rubber sheet material of approximately ¼ inch thickness, the portion cut out to form central opening 23a may be retained as fitted rubber pad 32, shown in FIGS. 1 and 6, which serves as a manual pressure applicator accessory to tourniquet 10 in the manner hereinafter described.

The practical utility and operation of head tourniquet 10 will now be apparent and is described, by way of example of, but not limited to, an excision of a donor strip of hair follicle bearing skin for transplanting. Tourniquet 10 may first be sized to loosely fit the patient's head by adjustment of tapes 25 to equal lengths so that sections 11 and 20 are centered diametrically opposite each other. In practice, the patient's head H may be bandaged and tourniquet 10 positioned over the bandages. However, for purpose of clarity the bandages have been omitted from FIGS. 3, 4 and 5. With tourniquet 10 positioned on the patient's head H so that the desired surgical work area A is exposed in window 21a, 23a of hemostatic frame section 20, worm gears 28 are alternately tightened to provide a snug fit. The bandage in the window 21a, 23a may then be cut away to expose the scalp on which the hair had previously been cut to the desired length in accordance with the hair transplant technique. Rubber pad 32 is then positioned in window 21a, 23a and manual pressure applied thereto for a period of time to substantially completely drain all blood from the underlying vessels in the scalp of area A. While maintaining pressure on pad 32, bladder 15 is inflated by means of bulb 16 to a pressure, indicated on gauge 17, 10 mm above the patient's systolic blood pressure. Pad 32 is then removed from window 21a, 23a to obtain complete accessibility to work area A aided by the low profile of frame section 20 which projects less than ¼ inch above the surface of the scalp. Work area A is now maintained as a bloodless field by the flexibility of frame 21 and liner 23 and the firm resiliency of liner 23 which, under the pressure exerted by inflated section 11, conforms to the contour of the skull and applies an equal pressure along the entire periphery of area A. Tapes 25 being spaced from the scalp permit blood circulation to other areas thereof.

The hair transplant technique herein illustrated contemplates the use of a stainless steel template 30 sized and shaped to conform to the exact dimensions of the donor strip to be excised and having a pair of openings 30a adjacent opposite tapered ends 30b thereof. As shown in FIG. 3, template 30 is positioned on area A to overlie the portion of the scalp to be excised and is secured thereto by fixation tacks 31 extending through openings 30a into the patient's skull. The outline of template 30 is then carefully traced with scalpel or marker, template 30 removed and the surgical removal of the donor strip as outlined performed, resulting in the excised area E, shown in FIG. 4, which requires closing. However, before closing and suturing it may be desirable to locate and tie or coagulate any relatively large vessels which may have been cut. This is readily accomplished by releasing the air pressure in bladder 15 by means of the release valve which is controlled by thumb screw 16b. After the large vessels have been ligated or coagulated, bladder 15 is again inflated to its previous pressure and the opposite longitudinal frame portions 21b grasped and manually urged medially as shown by the arrows in FIG. 5. The deflection of the longitudinal frame portions 21b toward each other is facilitated by a slight outward bowing of the opposite transverse frame portions 21c. As longitudinal frame portions 21b are medially deformed, the corresponding longitudinal sides 23b of liner 23 underlying frame portions 21b frictionally grip the upper and lower borders of area A and, as the scalp stretches, bring the opposite longitudinal edges of excised area E together along a straight line S. This deflected position of longitudinal frame portions 21b is maintained while the edges are sutured or staples applied to provide a straight line closure in accordance with well known surgical technique. Since the width of template 30 and hence excised area E does not exceed approximately 2 cm, the scalp will easily stretch the required amount to effect the desired closure. The pressure in bladder 15 is then released, tapes 25 loosened and tourniquet 10 removed from head H. To avoid fabric covering 18 becoming splattered with blood during the ligation procedure of the larger blood vessels, an appropriate plastic sheet covering, such as saran, may be used to wrap pneumatic section 11. Prior to use, tourniquet 10, template 30, fixation tacks 31, rubber pad 32, the plastic wrapping for section 11 and the wrench or screwdriver for manipulating worm gears 28 are all properly sterilized, as for example, by gassing.

The head tourniquet providing a bloodless field on the scalp and having incision closing capability while in position herein disclosed is seen to achieve the several objects of the invention and to be well adapted to meet conditions of practical use. As various possible embodiments might be made of this invention, and as various changes might be made in the disclosed tourniquet, it is to be understood that all matter herein set forth or shown in the accompanying drawings is to be interpreted as illustrative and not in a limiting sense.

What is claimed is:

1. A tourniquet for controlling hemostasis in a predetermined area of the scalp formed as a head encircling band comprising two flexible non-fabric plate members, each having a firmness for maintaining a predetermined substantially configuration, said plate members being arranged opposite each other and interconnected at opposite ends thereof by a pair of circumference size-adjusting means, a first of said plate members forming a backing and support for an air bladder having an air pressure gauge and valved, hand operated air pump bulb, the second of said plate members being formed as a frame having a large center opening, and a firm flexible and resilient rubber pad liner having a center opening conforming to said frame center opening, said liner being attached to the interior side of said frame with said frame and liner openings in register to provide a window exposing said predetermined scalp area, said plate member flexibility and firmness enabling said frame and liner to conform to the contour of the head for applying a substantially uniform hemostatic pressure to the periphery of said scalp area by pressure exerted by said air bladder.

2. The tourniquet defined in claim 1 in combination with a removable rubber pad fitted to said window for application of manual pressure to said predetermined area of the scalp to drain the blood therefrom preparatory to applying pressure to the frame and liner by inflation of said air bladder.

3. The tourniquet and rubber pad defined in claim 2 in which said rubber pad is the portion removed from said liner in forming said liner opening.

4. The tourniquet defined in claim 1 in which said frame and liner have opposite longitudinal frame portions, the latter being deflectable toward each other when said tourniquet is in operative position on a patient's head whereby the underlying scalp is moved to close an incision in said predetermined scalp area.

5. The tourniquet defined in claim 1 in which said second plate member and each of said size-adjusting means is pivotally connected enabling the second plate member to swingably adjust with respect to the longitudinal axis of said first plate member.

6. The tourniquet defined in claim 1 in which each of said size-adjusting means comprises an adjustable length strip element connected to an end of said first plate member having worm gear engaging spaced transverse slots, a fixed length strip element pivotally mounted to an end of said second plate member, a worm gear assembly mounted on a free end of said fixed length strip element engaging and feeding therethrough said adjustable length strip element, said worm gear assembly including a worm gear having a manipulatable head with manual tool engaging means facing said second plate member.

7. The tourniquet defined in claim 6 in which said pivotal mounting of said fixed length strip element includes a link formed with a central opening having a length exceeding the width, said fixed length strip element having a neck portion sized to fit widthwise through said opening and being formed inwardly of a wider end portion sized to fit diagonally through said link opening for assembly therewith, said link being secured to an end of said second plate member with an end portion of the latter overlapping an end of said link central opening thereby shortening said diagonal dimension to prevent passage of said wider end portion therethrough.

* * * * *

UNITED STATES PATENT AND TRADEMARK OFFICE
CERTIFICATE OF CORRECTION

PATENT NO. : 4,210,147
DATED : July 1, 1980
INVENTOR(S) : Jack Nestor and John W. Devine, Jr.

It is certified that error appears in the above—identified patent and that said Letters Patent is hereby corrected as shown below:

On the title page, Item [75], should read

---Jack Nestor, Miami Beach, Fla.;
John W. Devine, Jr., Miami, Fla.----

In column 6, line 8, delete "substantially".

Signed and Sealed this

Third Day of November 1981

[SEAL]

Attest:

GERALD J. MOSSINGHOFF

Attesting Officer        Commissioner of Patents and Trademarks